(12) United States Patent
Anzellini (10) Patent No.: US 7,384,389 B2
(45) Date of Patent: Jun. 10, 2008

(54) PARADOXICAL FLOW VALVE OF THE HEART

(75) Inventor: Fernando Anzellini, Calle 83 No 19-36 office 704, Bogota (CO)

(73) Assignee: Fernando Anzellini, Bogata (CO)

( * ) Notice: Subject to any disclaimer, the term of this patent is extended or adjusted under 35 U.S.C. 154(b) by 695 days.

(21) Appl. No.: 10/321,983

(22) Filed: Dec. 19, 2002

(65) Prior Publication Data

US 2004/0122282 A1    Jun. 24, 2004

(51) Int. Cl.
*A61M 1/12* (2006.01)
(52) U.S. Cl. .......................................... 600/16
(58) Field of Classification Search ................... 600/16; 604/9; 606/153
See application file for complete search history.

(56) References Cited

U.S. PATENT DOCUMENTS

| | | | |
|---|---|---|---|
| 4,192,302 A | 3/1980 | Boddie | |
| 4,503,568 A | 3/1985 | Madras | |
| 4,685,446 A | 8/1987 | Choy | |
| 4,712,551 A | 12/1987 | Rayhanabad | |
| 4,731,055 A | 3/1988 | Melinyshyn | |
| 4,861,336 A | 8/1989 | Helzel | |
| 5,006,104 A | 4/1991 | Smith | |
| 5,456,714 A | 10/1995 | Owen | |
| 5,545,215 A | 8/1996 | Duran | |
| 5,879,321 A | 3/1999 | Hill | |
| 6,045,531 A | 4/2000 | Davis | |
| 6,076,529 A | 6/2000 | Vanney | |
| 6,270,526 B1 | 8/2001 | Cox | |
| 6,290,728 B1 | 9/2001 | Phelps | |
| 6,881,199 B2 * | 4/2005 | Wilk et al. | 604/9 |

* cited by examiner

*Primary Examiner*—Carl Layno
*Assistant Examiner*—Eric D. Bertram (57) ABSTRACT

A method for transferring oxygenated blood from a low pressure chamber to a high pressure chamber includes placing a conduit between the left auricle and the aorta of a patient, attaching a prosthetic valve at the aortic end of the conduit, filling the conduit with oxygenated blood from the left auricle and using the downward systolic force of blood in the aorta to create a Venturi effect in the aorta allowing the oxygenated blood in the conduit to flow from the low pressure chamber into the high pressure chamber.

2 Claims, 6 Drawing Sheets

PARADOXICAL FLOW VALVE OF THE HEART

CROSS REFERENCE TO RELATED APPLICATIONS

Not applicable

BACKGROUND FIELD OF INVENTION

The paradoxical flow valve relates to a valved conduit that enables the passage of fluid between a low pressure chamber, the left auricle, and a high pressure chamber, the aorta, in order to obtain incremental flow of oxygenated blood in the high pressure chamber without the need to increase the force of the left ventricle myocardial pump or replace it by a mechanical or natural heart.

BACKGROUND DESCRIPTION OF PRIOR ART

There are many valves involved in the chambers of the heart. Prosthetic valves placed in heart chambers replacing a damaged normal valve is a common procedure. These prosthetic valves are usually placed in the original chamber when the native and damaged valve has to be replaced and are usually placed with the opening and closure mechanism following the normal pattern of blood flow within the heart.

There are also many devices used as a pump within the heart including the totally artificial heart that pumps blood in to the systemic circulation when the original heart fails as a pump because of disease or trauma.

There is the need for an impelling force to deliver blood from a low pressure chamber to a high pressure one and for this task too many devices have been used.

U.S. Pat. No. 6,290,728 Sep. 18, 2001 issued to Inventors Phelps; David Y. (Louisville, Ky.); Furnish; Greg R. (Louisville, Ky.); Hall; Todd A. (Goshen, Ky.); Griffin; Mark (Louisville, Ky.); Wolf; Scott J. (Minneapolis, Minn.); Wilk; Peter J. (New York, N.Y.); Schmelter; Jay (Plymouth, Minn.); Furnish; Simon (Louisville, Ky.) Asignee Percardia, Inc. (Nashua, N.H.)

A conduit is provided to provide a bypass around a blockage in the coronary artery. The conduit is adapted to be positioned in the myocardium or heart wall to provide a passage for blood to flow between a chamber of the heart such as the left ventricle and the coronary artery, distal to the blockage. The stent is self-expanding or uses a balloon to expand itself in the heart wall. Various attachment are provided to anchor the stent and prevent its migration. This conduit is not valved and delivers blood from a high pressure chamber to a low pressure chamber the coronary lumen.

U.S. Pat. No. 6,270,526 Aug. 7, 2001 issued to Inventors Cox; James L. (Ladue, Mo.) Asignee 3F Therapeutics, Inc. (Lake Forest, Calif.)

A method is disclosed for using tubular material to replace a semilunar heart valve (i.e., an aortic or pulmonary valve). To create such a replacement valve, the native valve cusps are removed from inside an aorta or pulmonary artery, and the inlet end of a tubular segment is sutured to the valve annulus. The outlet (distal) end of the tube is either "tacked" at three points distally, or sutured longitudinally along three lines; either method will allow the flaps of tissue between the suture lines to function as movable cusps. This approach generates flow patterns that reduce turbulence and closely duplicate the flow patterns of native semilunar valves. An article of manufacture is also disclosed, comprising a sterile biocompatible synthetic material which has been manufactured in tubular form, by methods such as extrusion or coating a cylindrical molding device, to avoid a need for a suture line or other seam to convert a flat sheet of material into a tubular shape.

The synthetic tube is packaged within a sealed watertight enclosure that maintains sterility of the tube. In this patent a tubular material is used in a replacement valve where the native cusps are removed and is not intended to deliver blood flow from a low pressure chamber to a high pressure chamber in a paradoxical flow pattern by means of a conduit with a mechanical valve at one end that achieves this purpose.

U.S. Pat. No. 5,006,104 Apr. 9, 1991 issued to Inventors Smith; William A. (Lyndhurst, Ohio); Chen; Ji-Feng (Cleveland, Ohio) Asignee: The Cleveland Clinic Foundation (Cleveland, Ohio)

A blood pump is disclosed that is useful as a ventricle assist or replacement device comprising a housing having a blood chamber and inlet and outlet ports for the ingress and egress of blood to and from the chamber. A deflectable diaphragm comprises a wall of the blood chamber which upon deflection collapses the blood chamber to urge blood from the chamber out through the outlet port. A pusher plate is disposed in association with the diaphragm. The pusher plate includes a collapsible guide mechanism which guides the plate from a first fill position to a second eject position. The guide mechanism may comprise a telescopic guide or straight-line linkage which is collapsible to a first fill position to occupy a substantially lesser space in the housing than when extended to second eject position. The guide mechanism avoids the need for a projection from the housing to accommodate the stroke of a guide mechanism. The guide mechanism can be independent of or combined with the drive means. In this patent the blood is delivered by a pump that is useful as a ventricle assist or replacement device removed and is not intended to deliver blood flow from a low pressure chamber to a high pressure chamber in a paradoxical flow pattern by means of a conduit with a mechanical valve at one end that achieves this purpose.

U.S. Pat. No. 4,685,446 Aug. 11, 1987 issued to Inventors Choy; Daniel S. J. (892 Riverbank Rd., Stamford, Conn. 06903)

A left ventricular assist device consisting of a balloon inflated and deflated sequentially to coincide with ventricular systole and diastole, respectively, placed within the left ventricle, thereby augmenting ejection of blood. In this patent there is a ventricular assist device with a balloon and is not intended to deliver blood flow from a low pressure chamber to a high pressure chamber in a paradoxical flow pattern by means of a conduit with a mechanical valve at one end that achieves this purpose.

U.S. Pat. No. 5,545,215 Aug. 13, 1996 issued to Inventors Duran; Carlos G. (Wellington Court 116 Knightsbridge, London SW1, GB)

A frame to be placed as an external support of a biological valved conduit containing three leaflets. This external frame, made of biocompatible metal or plastic is sutured to the outer surface of the valved conduit made of biological or biocompatible membrane or sigmoid valve root in order to maintain its natural geometry. The frame has a general cylindrical configuration, circular as viewed from above and below. From a side view however, both upper and lower ends of the cylinder present three convex curvatures joined at equidistant points of the circumference. These upper and lower curves are joined by three vertical struts, so that three large saddle-shaped paraboloid gaps result. The frame is a wire-like structure that perfectly follows the anatomical shape of the three sinuses of Valsalva, i.e. it corresponds to the external aspect of the line of implantation of the three sigmoid cusps below and the curved line of the sino-tubular junction above. The three vertical struts correspond to the three commissural areas. The frame is designed to be placed on the external surface of a valved conduit or a sigmoid valve root and therefore does not interfere with the natural movements of the three cusps and does not enter in contact with the circulating blood stream. The valved conduit is made of biological or biologically compatible membrane with three bulges corresponding to the three sinuses of Valsalva and three leaflets. In this patent there is a frame to be placed as an external support of a biological valved conduit containing three leaflets The frame is designed to be placed on the external surface of a valved conduit or a sigmoid valve root and is not intended to deliver blood flow from a low pressure chamber to a high pressure chamber in a paradoxical flow pattern by means of a conduit with a mechanical valve at one end that achieves this purpose.

U.S. Pat. No. 6,045,531 Apr. 4, 2000 issued to Inventors Davis; Albert (Richardson, Tex.) Asignee: Chase Medical Inc. (Richardson, Tex.)

A catheter and method of use adapted to intermittently deliver fluids to and drain fluids from a body vessel having an interior lumen occluding balloon. The selective inflation and deflation of the inner balloon controls the occlusion or communication of an inner lumen. The inner occluding balloon is defined between the distal end of the catheter and a proximal lumen opening allowing for the selective isolation of the proximal openings from the catheter distal end. The catheter of the present invention and several methods of use thereof are ideally suited for aortic perfusion and providing myocardial infusion in antegrade fashion using a single lumen. The catheter is further provided with a double lobed outer balloon for selectively occluding the body vessel, such as the aorta, and to provide a bloodless region to complete the proximal end of an anastomosis while perfusing the myocardium to restart the heart. In this patent a method issued to deliver fluids intermittently to and drain fluids intermittently from a body vessel having an interior lumen occluding balloon and for aortic perfusion and is not intended to deliver blood flow from a low pressure chamber to a high pressure chamber in a paradoxical flow pattern by means of a conduit with a mechanical valve at one end that achieves this purpose.

U.S. Pat. No. 5,879,321 Mar. 9, 1999 issued to Inventors Hill; Bradley B. (Lexington, Ky.)) Asignee: The University of Ky. Research Foundation (Lexington, Ky.)

A shunt includes a tubular body having first and second legs at a proximal end and a third leg at a distal end. A fluid distensible balloon and cooperating insufflation conduit are carried on the tubular body. The first leg of the tubular body includes a longitudinal slit for receiving the second leg whereby the first and second legs may be positioned substantially coaxial so as to allow easier introduction of the shunt into the blood vessel of a patient. Similarly, the second leg having a longitudinally slit for receiving a portion of the cooperating insufflation conduit and also holding it in a coaxial position. A leader tube with a blunt atraumatic tip is received over the proximal end of the tubular body to further aid in the introduction of the shunt. In this patent the shunt is a tubular body with a fluid distensible balloon and is not intended to deliver blood flow from a low pressure chamber to a high pressure chamber in a paradoxical flow pattern by means of a conduit with a mechanical valve at one end that achieves this purpose.

U.S. Pat. No. 4,503,568 Mar. 12, 1985 issued to Inventors Madras; Peter N. (Newton, Mass.) Asignee: New England Deaconess Hospital (Boston, Mass.)

A arterial bypass includes a relatively large diameter proximal tubular segment for connection to the upstream portion of an artery and a relatively small diameter distal tubular segment for connection to the downstream portion of the artery. A tapered adapting segment joins the proximal and distal segments. The distal segment is coupled to the downstream portion of the artery by way of a connector element. The connector element includes an entrance member, a coupled, angularly offset exit member and a heel member. The exit and heel members are adapted for insertion through an arteriotomy and into the vessel. The exit member outer diameter is matched to the vessel inner diameter near the arteriotomy. In this patent an arterial bypass includes a relatively large diameter proximal tubular segment for connection to the upstream portion of an artery and a relatively small diameter distal tubular segment for connection to the downstream portion of the artery and is not intended to deliver blood flow from a low pressure chamber to a high pressure chamber in a paradoxical flow pattern by means of a conduit with a mechanical valve at one end that achieves this purpose.

U.S. Pat. No. 6,076,529 Jun. 20, 2000 issued to Vanney; Guy P. (Blaine, Minn.); Tweden; Katherine S. (Mahtomedi, Minn.) Asignee Heartstent Corporation (St. Paul, Minn.)

A transmyocardial implant includes a hollow conduit inserted through a heart wall. The conduit defines a blood flow path between a heart chamber opening and a vessel opening. The heart chamber opening of the conduit is placed in communication with a chamber of the heart. A coronary vessel on an exterior of the heart wall is severed into a proximal portion and a distal portion. The distal portion of the vessel is placed into the vessel opening of the conduit. An alternative embodiment places the vessel flush with the vessel opening of the conduit. In this patent the conduit defines a blood flow path between a heart chamber opening and a vessel opening like in our invention but involves a coronary artery and is not intended to deliver blood flow from a low pressure chamber to a high pressure chamber in a paradoxical flow pattern by means of a conduit with a mechanical valve at one end that achieves this purpose.

U.S. Pat. No. 4,192,302 Mar. 11, 1980 issued to Boddie; Arthur W. (San Antonio, Tex.) Asignee for the Government for governmental purposes.

Hepatic isolation and perfusion circuit assembly The assembly, through a plurality of shunts, allows blood circulation from the lower part of a patient's body and from the intestines to flow unimpeded to the heart, while isolating hepatic venous blood containing toxic agents from the general circulation and returning it to a heart-lung machine. As a result, the assembly can be used to perfuse the liver, of a patient which has become involved with cancer, with extremely high does of cancericidal chemotherapy agents, while at the same time avoiding the toxic effects of these agents on the patient's body as a whole. In this patent the assembly can be used to perfuse the liver and is not intended to deliver blood flow from a low pressure chamber to a high pressure chamber in a paradoxical flow pattern by means of a conduit with a mechanical valve at one end that achieves this purpose.

U.S. Pat. No. 4,712,551 Dec. 15, 1987 issued to Rayhanabad; Simon B. (Long Beach, Calif.)

A vascular shunt is employed for use in surgical by-pass operations to divert blood flow during an operation from the aorta into a plurality of arteries serving different organs of the body. The vascular shunt is comprised of a hollow, flexible inlet tube with an inlet tip projecting there from and turned to form an inlet mouth. The tip is adapted for insertion into an incision surgically formed into the wall of a human aortic artery so that the mouth of the inlet tip is directed upstream into the aorta. A releasable inlet sealing means is connected to the inlet tip to lock blood flow in the aorta downstream beyond the inlet tip. Tubular branches emanate from the inlet tube. Each branch is of a smaller internal cross-sectional area than the inlet tube and is adapted for connection to an artery serving an organ of the human body. In this patent A vascular shunt is employed to divert blood flow during an operation from the aorta into a plurality of arteries serving different organs of the body and not from the heart to the aorta by-passing the muscular chamber of the left ventricle.

U.S. Pat. No. 4,731,055 Mar. 15, 1988 issued to Melinyshyn; Lev A. (Mt. Prospect, Ill.); Stupar; Jeffrey M. (Chicago, Ill.); Goldberg; Edward M. (Glencoe, Ill.) Asignee Becton, Dickinson and Company (Franklin Lakes, N.J.)

A improved blood flow conduit provided with external inflatable balloons and having rigid end portions for facilitating insertion into blood vessels and means for detecting pulsatile flow in the conduit and excessive pressure in the balloons. In this patent there is no shunt or paradoxical blood flow intended to by-pass the heart pump by means of a conduit with a mechanical valve at one end that achieves this purpose.

U.S. Pat. No. 4,861,336 Aug. 29, 1989 issued to Heizel; Manfred W. (Frankenstrasse 29, 8700 Wurzburg, Del.)

A puncture catheter for transjugular or transfemoral percutaneous introduction into the lower vena cava is described. The catheter is composed of an outer direction catheter (1) and an inner puncturing catheter (5) introduced into it. The end segment (2) of the direction catheter (1) may be bent at an angle by means of a pulling mechanism (4), and directed toward the wall of the vena cava (V1). The tip of the puncture catheter (5) serves to perforate the wall of the vena cava (V1) and to puncture the portal vein (VP) ventrally crossing the vena cava (VCI). This non-anatomical connection is stabilized by accessory parts, a so-called porto-caval shunt. In this patent a puncture catheter for transjugular or transfemoral percutaneous introduction into the lower vena cava is described and is not intended to deliver blood flow from a low pressure chamber to a high pressure chamber in a paradoxical flow pattern by means of a conduit with a mechanical valve at one end that achieves this purpose.

U.S. Pat. No. 5,456,714 Oct. 10, 1995 issued to Owen; Earl R. (Surry Hills, NSW 2010, AU)

A tubular surgical implant for joining to a wall of a vessel or hollow organ is disclosed such that the implant opens into the interior of the vessel or organ. The implant has an open ended tube, a deformable flange at one end of the tube, a plurality of spikes extending from the flange, alongside and generally parallel to the tube, and a locking ring arranged to slide axially on the tube, the locking ring incorporating a plurality of holes aligned with and adapted to received the spikes in this patent a tubular surgical implant for joining to a wall of a vessel or hollow organ is disclosed such that the implant opens into the interior of the vessel or organ but there is no valve involved to achieve the goal of paradoxical flow pattern by means of a conduit with a mechanical valve at one end.

SUMMARY

The object of the PARADOXICAL FLOW VALVE is to provide a device capable of transferring oxygenated blood flow from a low pressure chamber like the left auricle to a high pressure chamber such as the aorta through a valved tube skipping a damaged left ventricular pump in a diseased heart with impairment in its impelling force thus bypassing the contractile force of the heart and augmenting the availability of oxygenated blood to the economy. The valve at the end of the tube implanted in the aorta exerts the function of impeding the return of blood from the high pressure flow chamber to the low pressure flow chamber and facilitates the passage of oxygenated blood.

OBJECTS AND AN ADVANTAGES

Accordingly, the main object and advantages of the PARADOXICAL FLOW VALVE is for a system that allows blood flow to be transferred from a low pressure chamber to a high pressure chamber by means of a valved tube attached from the left auricle to the wall of the descending aorta where a valve with a mechanism that comprises two leaflets and two or more pivot springs which allows oxygenated blood flow to pass directly from the left auricle to the general economy without the need of an impending force from the left ventricle of the heart that when is affected by disease cannot achieve this natural function completely. The low ejection fraction of the left ventricle is one of the major public health problems in the world, as supported by thousands of papers and studies all over the world.

Many other devices that replace the natural left ventricle pump have been invented including the total heart transplantation, but there is no perfect device or method that actually achieves this goal and the quality of life of these patients is greatly affected, thus there is the need for a method that can improve quality of life for millions of persons that suffer from this condition, as augmenting periferical oxygenated natural blood flow from one chamber to another in the less traumatic way in order to improve quality of live is essential.

It is yet another object of the PARADOXICAL FLOW VALVE to provide a system capable of improving the quality of life of patients affected by low ejection fraction from the left ventricle of the heart, that helps to reduce dramatically the outcome and prognosis of one of the leading causes of death and deterioration of quality of life, without the need of mechanical devices powered by external or internal sources of energy that are not eternal, or heart transplantation either partial of total, both of which have very well-known problems regarding quality of life and mortality.

These and other purposes of the PARADOXICAL FLOW VALVE are achieved by means of the embodiment of a valve in a tube with a special mechanism to ensure that blood cannot enter in a retrograde way from a high pressure cavity to a low pressure cavity Another object of the PARADOXICAL FLOW VALVE is to provide a method to evacuate blood via a Venturi effect into the stream of the aorta, a high pressure cavity, during left ventricular ejection systole in order to augment the availability of oxygenated blood in this cavity.

It is a further object of the PARADOXICAL FLOW VALVE to provide a mechanism that prevents blood from entering in a retrograde way to the left auricle, a low pressure cavity, either in systole or diastole that can be deleterious for the normal physiologic functioning of the heart It is yet another object of the PARADOXICAL FLOW VALVE to provide a mechanism in the end of a conduit that triggered by means of the heart systole provides an opening within the aorta lumen of a leaflet in a way that by a Venturi mechanism blood is trespassed smoothly from the conduit, previously filled with blood in a physiological way from the left auricle, to the lumen of the aorta significantly increasing the amount of blood that reaches the systemic circulation.

It is yet another object of the PARADOXICAL FLOW VALVE to provide a mechanism in the end of a conduit that triggered by means of the heart diastole provides a closure within the aorta lumen of a leaflet in order to prevent blood from returning in a retrograde way to the conduit and then to the left auricle, a low pressure chamber.

Finally, the PARADOXICAL FLOW VALVE is designed to help a patient with a low ejection fraction of a diseased heart to transfer oxygenated blood to the systemic circulation from a low pressure chamber, the left auricle, to a high pressure chamber, the aorta, with out the need of increasing the contractile work of the heart, that affected by disease or trauma, cannot achieve this goal and therefore alleviating the systemic economy from the consequences of a catastrophic low ejection fraction.

These and other purposes of the PARADOXICAL FLOW VALVE are achieved by means of the embodiment of a two leaflet valve in the aortic end of a conduit that transfers oxygenated blood from the left auricle to the aorta lumen. The PARADOXICAL FLOW VALVE that is implanted in the distal end anastomosis of the tube that opens in the descending aorta lumen, has a fixed superior leaflet and a mobile inferior leaflet connected to an aileron that protrudes superiorly and is struck on its internal surface by the stream of blood in systole triggering a paradoxical opening effect of the inferior implanted leaflet that has two or more pivot springs, each pivot is connected to permit the leaflet to pivot with minimal resistance between an open and closed orientation, attached to its inner surface, allowing the passage of blood flow through a well-known Venturi effect that is triggered within the aorta lumen when anterograde blood flow descends within the aorta lumen to the distal economy. The tube that is previously filled with oxygenated blood from the left auricle empties at least fifty percent its blood content in the aorta lumen by means of this Venturi effect triggered by the valve. When blood flow in diastole moves in a retrograde way within the aorta lumen it strikes the inferior part of the valve that is connected via a double lumen mechanism to the aileron exerting the effect of a pivotal force that augments the force necessary to close the valve in diastole, taking in account that blood returning in diastole first finds the inferior part of the valve, and then the external face of the aileron that is part of the inferior leaflet, triggering the closing of this leaflet with the pivot spring acting in a reverse way and therefore impeding the flow of blood into the valved tube that has a lower pressure, similar to that in the left auricle, and achieving the goal of transferring through a reversal mechanism, blood from a low pressure chamber to a high pressure chamber without the need of a pump.

There is great medical health concern as to the treatment of low ejection fraction of the heart, given that there is a large proportion of patients that, because of suffering from this condition, have the need of a mechanical pump that replaces the left ventricle, or a heart transplantation, or a total artificial mechanical heart. If a proper way to transfer oxygenated blood from a low pressure chamber camera, like the left auricle, to a high pressure chamber, the aorta, without the need of an artificial or natural implanted pump is achieved, the outcome of millions of patients with heart failure and low ejection fraction consequences, can be improved dramatically It is for these cases that the PARADOXICAL FLOW VALVE is intended.

Further objects and advantages of our invention will become apparent upon consideration of the drawings and ensuing description.

DESCRIPTION OF DRAWINGS

In the drawings, closely related figures have the same number but different alphabetic suffixes.

REFERENCE NUMBERS IN DRAWINGS

5 PULMONARY VEINS
6 LEFT AURICLE
7 LEFT VENTRICLE
8 MITRAL VALVE
9 CONDUIT
10 PROXIMAL ANASTOMOSIS
11 DISTAL ANASTOMOSIS
12 PARADOXICAL FLOW VALVE
13 AORTA
14 AILERON
15 SUPERIOR FIXED LEAFLET
16 INFERIOR MOBILE LEAFLET
17 PIVOT SPRINGS
18 AORTA LUMEN
19 INFERIOR PART OF THE VALVE
20 DOUBLE LUMEN

DETAILED DESCRIPTION OF THE INVENTION

Figure 1:
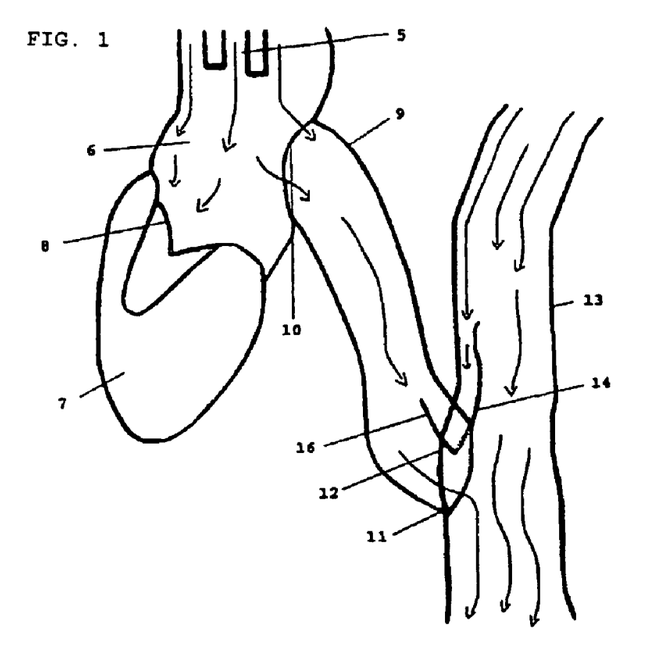
FIGS. 1 and 2 shows how the conduit is attached in the left auricle in order to obtain, as first presented, oxygenated blood from this chamber before entering the left ventricle through the mitral valve and the attachment to the wall of the descending aorta where the PARADOXICAL FLOW VALVE is placed
Figure 2:
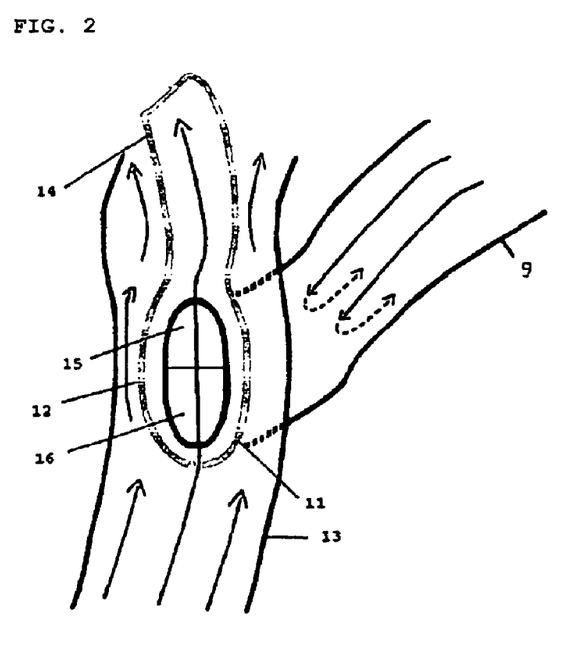

As illustrated in FIG. 1 and FIG. 2, when blood enters through the pulmonary veins 5 to the left auricle 6, the natural passage of blood flow to the left ventricle 7 through the mitral valve 8, is deviated in part to a conduit 9 attached to the wall of the auricle 6 taking in account that this proximal anastomosis 10 is first presented in the course of blood flow.

Figure 3A:
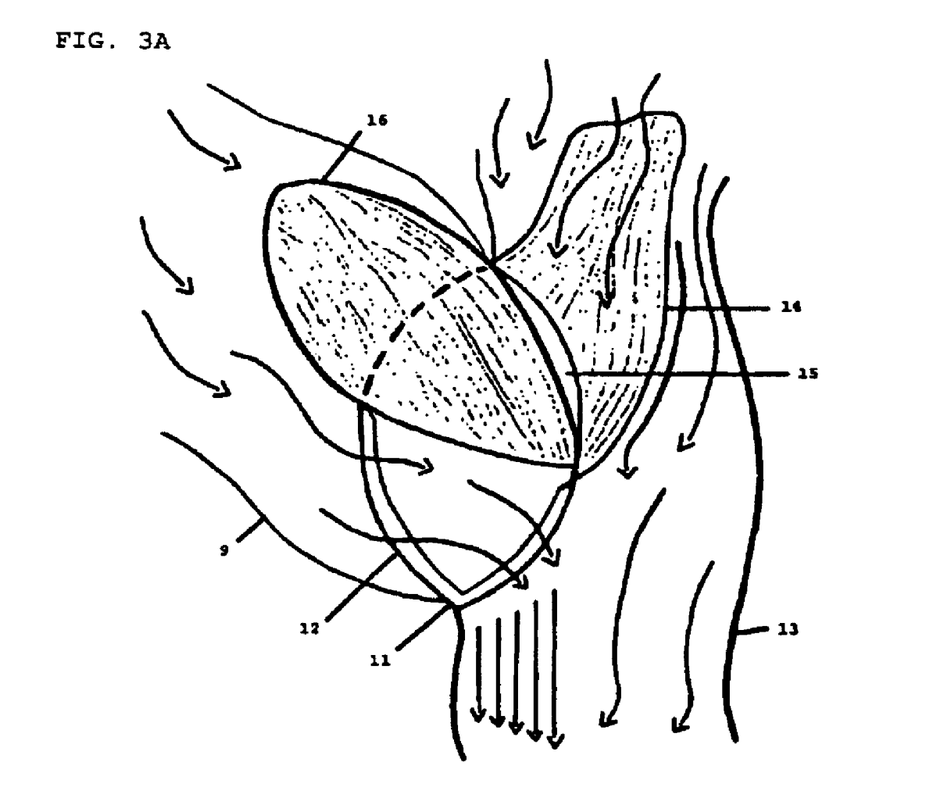
FIGS. 3A 3B and 3C shows how the inferior leaflet of the PARADOXICAL FLOW VALVE opens inside the conduit, as soon the aileron is struck between his internal surface and the wall of the aorta by the stream of blood in systole, diminishing the aorta lumen and thus triggering a Venturi effect in the lower insertion of the tube, that allows the passage of oxygenated blood into the lumen of the aorta augmenting the availability of blood flow into the general economy
Figure 3B:
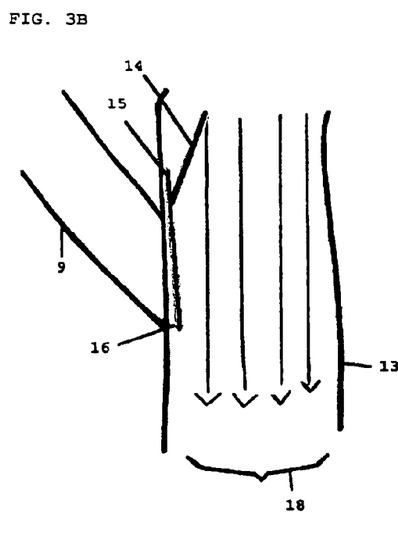
Figure 3C:
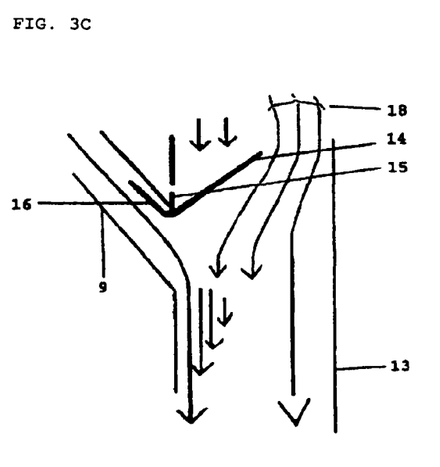
Figure 3D:
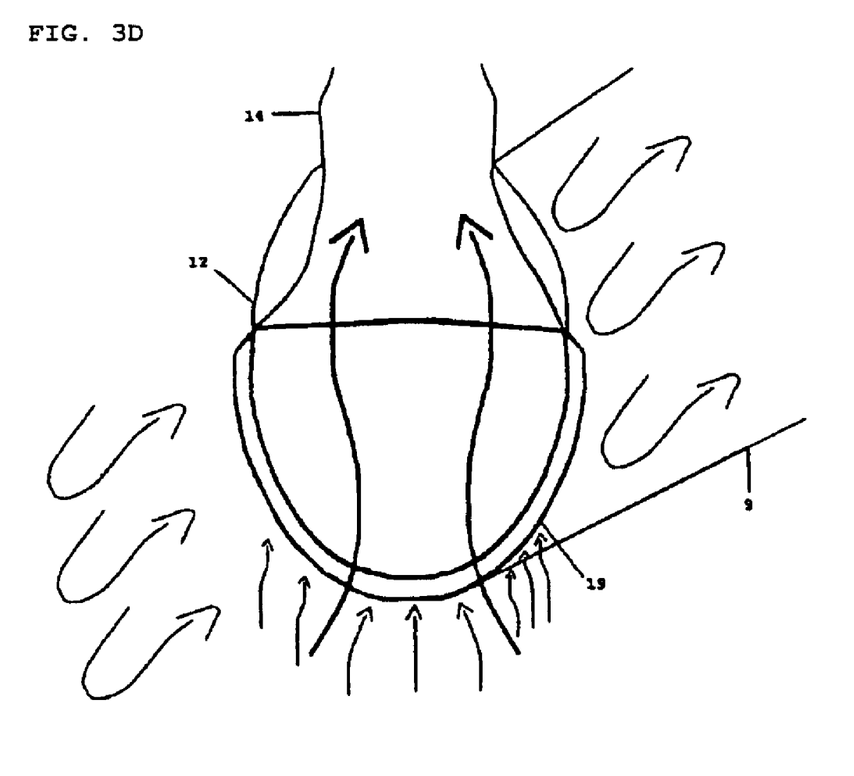
FIG. 3D shows the PARADOXICAL FLOW VALVE from the view within the aorta lumen, closed by the double force exerted when first the inferior part of the inferior leaflet gets contact with blood in diastole returning from the periphery and then when the same stream of blood makes contact with the external face of the aileron, which is also attached to the inferior leaflet.
Figure 4A:
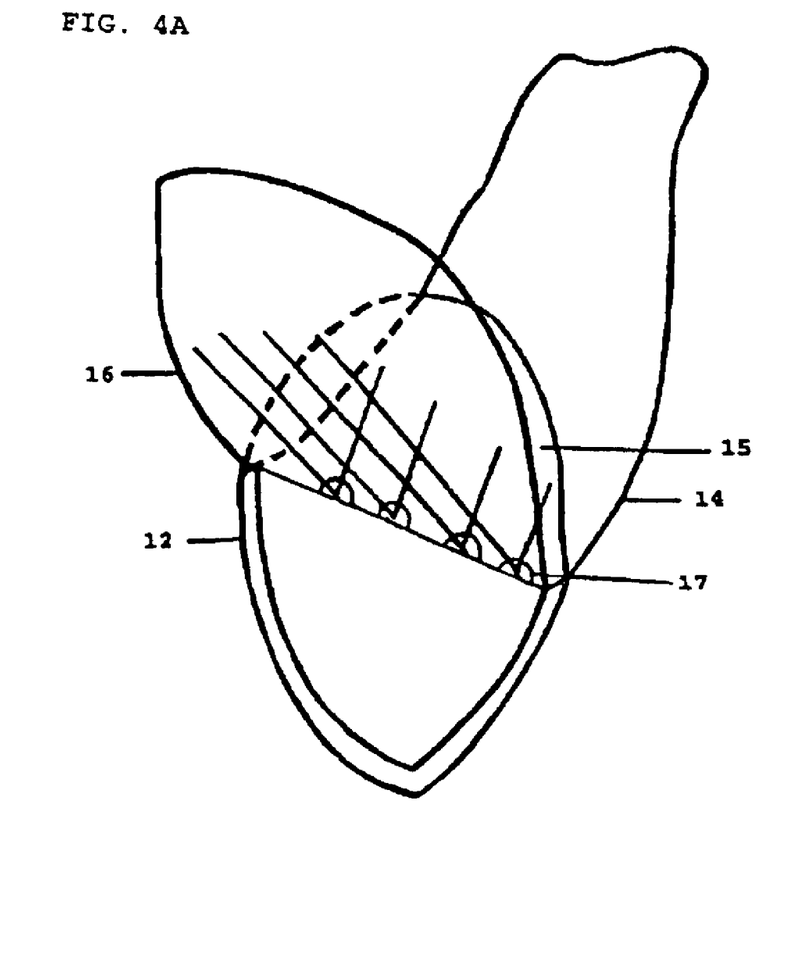
FIG. 4A shows the PARADOXICAL FLOW VALVE from the view within the conduit lumen, its inferior leaflet opened by means of the movement of the pivot springs attached to the surface of both the fixed portion of the valve, the superior leaflet, and to the mobile portion of the valve, the inferior leaflet.
Figure 4B:
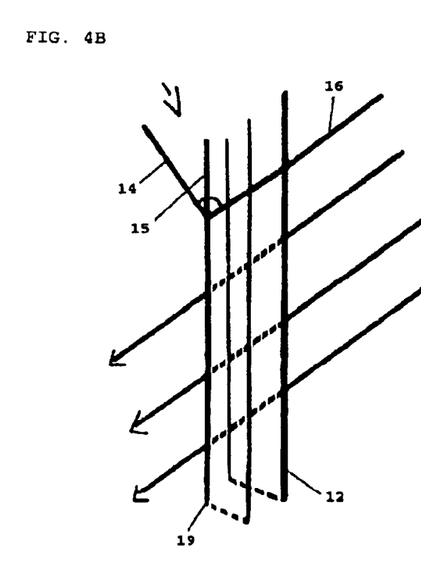
FIG. 4B shows the PARADOXICAL FLOW VALVE from a lateral view in an open position when blood in systole strikes the aileron between his inner surface and the aorta wall and the inferior double lumen mechanism in a closed position (paradoxical position) allowing the passage of oxygenated blood from the conduit to the aorta lumen
Figure 4C:
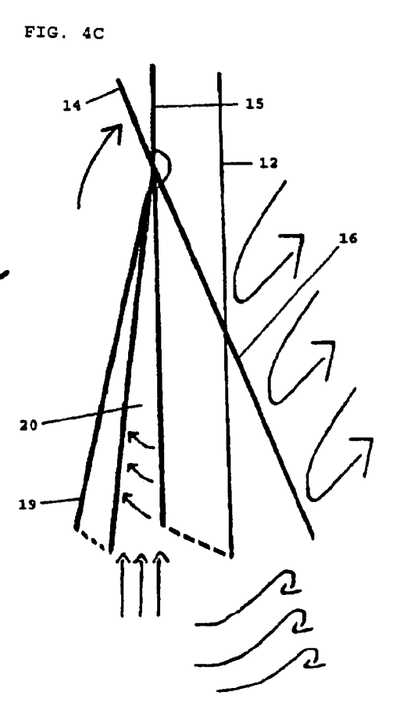
FIG. 4C shows the PARADOXICAL FLOW VALVE from a lateral view in a closed position when blood in diastole strikes the aileron between his external surface and the aorta wall and the inferior double lumen mechanism in a open position (paradoxical position) when blood in diastole returns within the aorta lumen and contacts the double lumen mechanism, impeding the return of blood from the aorta lumen to the conduit and thus to the left auricle from a high pressure chamber to a low pressure chamber.

As illustrated in FIGS. 3A 3B and 3C this conduit 9 with low pressure has previously evacuated its content protected from the high pressure distal end anastomosis 11 by the PARADOXICAL FLOW VALVE 12 that attached to the distal end of the conduit 9 opens when there is anterograde blood flow within the aorta 13, that is in some way diminished because of left ventricle 7 pump disease, and closes when retrograde blood flow in diastole contacts one of the parts 14, in order to increase in a substantial amount the availability of oxygenated blood to the economy and thus alleviating the clinical catastrophe of low ejection fraction because of a diseased pump 7 without the need of an artificial pump or heart.

The PARADOXICAL FLOW VALVE 12 that is implanted in the distal end anastomosis of the tube 11 that opens in the descending aorta lumen 18, has a superior fixed leaflet 15 and an inferior mobile leaflet 16 connected to an aileron 14 that protrudes superiorly and is struck in his internal surface by the stream of blood in systole triggering a paradoxical opening effect of the inferiorly implanted leaflet 16 that has two or more pivot springs 17 attached to his inner surface allowing the passage of blood flow through a well-known Venturi effect that is triggered when anterograde blood flow descends within the aorta lumen 18 to the distal economy The Venturi effect says that when the velocity of a fluid increases the pressure diminishes, (as in the Bernoulli equation $P+\frac{1}{2}pv2=constant$); taking in account that the radius of the aorta lumen 18 is changed by means of the movement of the aileron 14 the velocity of the fluid is increased after passing the contact zone with the aileron 14 so therefore the pressure diminishes in the aorta lumen 18, and according to the Venturi effect, oxygenated blood is allowed to pass from the conduit 9 to the aorta 13 in the zone of low pressure augmenting the quantity of available oxygenated blood to the systemic circulation.

The tube 9 that has been previously filled with oxygenated blood from the left auricle 6 empties at least fifty percent of his blood content in the aorta 13 by means of this Venturi effect triggered by the valve.

As illustrated in FIGS. 3D, 4A, 4B and 4C when blood flow in diastole moves in a retrograde way within the aorta lumen 18 it first strikes the inferior part of the valve 19 that is connected via a double lumen mechanism 20 to the aileron 14 exerting the effect of a pivotal force that augments the force necessary to close the valve 16 in diastole, taking in account that blood returning in diastole first finds the inferior part of the valve 19, and then the external face of the aileron 14 that is part of the inferior leaflet 16, thus triggering the closing of the inferiorly implanted leaflet 16 with the pivot spring 17 acting in a reversal way and therefore impeding the flow of blood into the valved tube 9 that has a lower pressure, similar to that in the left auricle, 6 and achieving the goal of transferring, through a reversal mechanism, blood from a low pressure chamber 6 to a high pressure chamber 13 without the need of a pump.

We believe that the PARADOXICAL FLOW VALVE can achieve the goal of transferring blood flow from a low pressure 6 camera to a high pressure camera 13 thus alleviating the need for many patients with a poor left ventricle pump for an artificial mechanical left ventricle pump, an artificial total heart, a heart transplantation or any other method intended to augment the availability of oxygenated blood in the aorta 13 and in the whole economy and this will alleviate the symptoms of millions of people that suffers the clinical consequences of a low ejection fraction of the heart.

Operation

The PARADOXICAL FLOW VALVE provide a device capable of transferring oxygenated blood flow from a low pressure chamber (like the left auricle 6) to a high pressure chamber (like the aorta 13) through a valved tube skipping a damaged left ventricular muscle in a diseased heart with impairment in its impelling force thus bypassing the contractile force of the heart and augmenting the availability of oxygenated blood to the economy.

When blood enters through the pulmonary veins to the left auricle the natural passage of blood flow to the left ventricle through the mitral valve is deviated in part to a conduit attached to the wall of the auricle, taking in account that this artificial anastomosis is first presented in the course of blood flow. The PARADOXICAL FLOW VALVE provide a device capable of transferring oxygenated blood flow from a low pressure chamber (like the left auricle 6) to a high pressure chamber (like the aorta 13) through a valved tube skipping a damaged left ventricular muscle in a diseased heart with impairment in its impelling force thus bypassing the contractile force of the heart and augmenting the availability of oxygenated blood to the economy.

The PARADOXICAL FLOW VALVE that is implanted in the distal end anastomosis of the tube that opens in the descending aorta lumen, has a superior fixed leaflet and an inferior mobile leaflet At least one leaflet is pivotably positioned in the flow path, for permitting flow in a forward direction and resisting flow in a reverse direction. The leaflet comprises a major axis which is perpendicular to and longer than a minor axis. Preferably, the leaflet comprises a wire frame in which at least two longitudinal struts extend generally along the direction of the major axis and are connected by a bend. The leaflet preferably comprises at least three or four struts extending generally along the direction of the major axis. The wire frame of the leaflet is provided with at least one and preferably two or more pivots which define an axis of rotation. Each pivot is connected to the tubular wire support, to permit the leaflet to pivot with minimal resistance between an open and closed orientation and connected to an aileron that protrudes superiorly and is struck in his internal surface by the stream of blood in systole, descending through the aorta, triggering a paradoxical opening effect of the inferiorly implanted leaflet allowing the passage of blood flow through a well-known Venturi effect that is triggered within the aorta lumen. According to the Venturi effect, oxygenated blood is allowed to pass from the conduit to the aorta in the zone of low pressure, obtained by the movement of the aileron, augmenting the quantity of available oxygenated blood to the systemic circulation.

The tube that has been previously filled with oxygenated blood from the left auricle empties his blood content in the aorta lumen by means of this Venturi effect triggered by the valve. When blood flow in diastole moves in a retrograde way within the aorta lumen it hits first the inferior part of the valve that is connected via a double lumen mechanism to the aileron exerting the effect of a pivotal force that augments the force necessary to close the valve in diastole, taking in account that blood returning in diastole first finds the inferior part of the valve, and then the external face of the aileron that is part of the inferior leaflet, thus triggering the closing of the inferiorly implanted leaflet with the pivot spring acting in a reversal way and therefore impeding the flow of blood into the valved tube that has a lower pressure, similar to that in the left auricle, and achieving the goal of transferring, through a reversal mechanism, blood from a low pressure chamber to a high pressure chamber, without the need of an pump using the remaining force of a diseased heart, the systole, to trigger the opening of a leaflet and the force of the systemic periferical resistance, the diastole, to trigger the closure of the same leaflet in order to obtain an increase in the availability of oxygenated blood in the general economy.

The device is able to transfer oxygenated blood from a low pressure chamber to a high pressure chamber by means of a valved tube with a distally implanted valve with a paradoxical movement thereof.

CONCLUSIONS, RAMIFICATIONS, AND SCOPE OF THE INVENTION

Thus the reader will see that oxygenated blood flow can be transferred from a low pressure chamber, the left auricle, to a high pressure chamber, the aorta, in the presence of a damaged pump, the left ventricle, through a valved conduit containing a valve that transforms the movement of blood in systole and diastole within the aorta lumen, even in the presence of a diseased heart, in a force that triggers a mechanism that opens a valve allowing the passage of blood in a paradoxical way, from low to high pressure chamber, and thus augmenting the availability of oxygenated blood to the general economy without the need of a pump or a artificial heart or a heart transplantation.

Although the above description contains many specificity's, these should not be construed as limiting the scope of the PARADOXICAL FLOW VALVE but rather as an exemplification of a preferred embodiment thereof. Many other variations are possible for example, the conduit may have other type (s) of connection (s) to another chamber (s) of the heart or to any other chamber (s) outside the heart, may have more than one valve, may allow for the passage of oxygenated blood trough any other mechanism by-passing the heart without the need of a mechanical pump or artificial or transplanted heart etc.

Thus the scope of the PARADOXICAL FLOW VALVE should be determined by the appended claims and their legal equivalents, rather than by the examples given.

The invention claimed is:

1. A method for transferring oxygenated blood from a low pressure chamber to a high pressure chamber, wherein the low pressure chamber is the left auricle and the high pressure chamber is the aorta, the method comprising:

placing a conduit between the left auricle and the aorta of a patient;

attaching a prosthetic valve at the aortic end of the conduit, wherein the valve comprises an aileron pivotally attached to an inferior mobile leaflet;

filling the conduit with oxygenated blood from the left auricle, wherein the blood is blocked from moving into the aorta by the original position of the inferior mobile leaflet;

using the downward systolic force of blood in the aorta to contact and push the aileron into the lumen of the aorta, wherein the pivot of the aileron decreases the internal area of the aorta, and wherein the pivot of the aileron causes the attached inferior mobile leaflet to pivot into the conduit and open a lumen between the conduit and the aorta; and creating a Venturi effect in the aorta by the decrease in area, wherein the Venturi effect allows the oxygenated blood in the conduit to flow from the low pressure chamber into the high pressure chamber.

2. The method of claim 1, wherein the inferior mobile leaflet and the aileron are both pivotally attached to a double lumen, the method further comprising:

using the returning diastolic force of blood in the aorta to make first contact with the double lumen, wherein the first contact triggers the first part of the closing movement of the inferior mobile leaflet; and using the returning force of blood in the aorta to make a second contact with the aileron following the first contact, wherein the second contact pushes the aileron to pivot out of the lumen of the aorta, and wherein the pivot of the aileron causes the attached inferior mobile leaflet to pivot back to its original position, closing the lumen between the conduit and the aorta, impeding the blood in the aorta from flowing back into the conduit, and thus preserving the normal pressure differential between the aorta and the left auricle.

* * * * *